(12) United States Patent
Shirahata et al.

(10) Patent No.: US 7,276,379 B2
(45) Date of Patent: Oct. 2, 2007

(54) DETECTION METHOD AND QUANTITATIVE ANALYSIS METHOD FOR HYDROGEN RADICAL

(75) Inventors: Sanetaka Shirahata, c/o Nihom Trim Co., Ltd., 1-8-34, Oyodonaka, Kita-ku, Osaka-shi, Osaka (JP); Kazumichi Otsubo, Osaka (JP)

(73) Assignees: Nihon Trim Co., Ltd., Osaki-shi (JP); Sanetaka Shirahata, Koga-shi (JP)

( * ) Notice: Subject to any disclaimer, the term of this patent is extended or adjusted under 35 U.S.C. 154(b) by 122 days.

(21) Appl. No.: 10/344,341

(22) PCT Filed: May 27, 2002

(86) PCT No.: PCT/JP02/05126

§ 371 (c)(1),
(2), (4) Date: Feb. 11, 2003

(87) PCT Pub. No.: WO02/097427

PCT Pub. Date: Dec. 5, 2002

(65) Prior Publication Data

US 2003/0186452 A1    Oct. 2, 2003

(30) Foreign Application Priority Data

May 29, 2001    (JP)    ............................. 2001-160915

(51) Int. Cl.
*G01N 33/00*    (2006.01)
(52) U.S. Cl. ...................................... 436/144
(58) Field of Classification Search ................. 436/144
See application file for complete search history.

(56) References Cited

U.S. PATENT DOCUMENTS 6,121,305 A    9/2000    Obara et al.

FOREIGN PATENT DOCUMENTS

| | | |
|---|---|---|
| GB | 2 107 863 A | 5/1983 |
| JP | 58-45557 A | 3/1983 |
| JP | 10-306077 A | 11/1998 |
| JP | 2001-324500 A | 11/2001 |
| RU | 2072999 C1 | 2/1997 |
| RU | 2094429 C1 | 10/1997 |
| WO | WO96/09540 A1 | 3/1996 |

OTHER PUBLICATIONS

Barr et al., J. Biol. Chem., Jun. 28, 1996, vol. 271, No. 26. pp. 15498-15503.

*Primary Examiner*—Jill Warden
(74) *Attorney, Agent, or Firm*—Birch, Stewart, Kolasch & Birch, LLP

(57) ABSTRACT

The invention is directed to a method of detecting hydrogen radicals present in water or an aqueous solution, characterized in adding sodium salt of 3,5-dibromo-4-nitrosobenzenesulfonic acid (DBNBS) to a sample for detecting the hydrogen radicals by coloring resulting from absorption characteristics thereof, and further characterized in blowing hydrogen gas into a solution of 1,1-diphenyl-2-piclylhydrazyl (DPPH) having absorption in the vicinity of 517 nm and a solution of sodium salt of 3,5-dibromo-4-nitrosobenzenesulfonic acid (DBNBS) at a constant speed in the presence of platinum black for quantitatively analyzing the concentration of the hydrogen radicals from a calibration curve C of a graph of correlation between absorbance in the vicinity of 450 nm derived from a DBNBS azo compound and the concentration of the formed hydrogen radicals.

3 Claims, 15 Drawing Sheets

HYDROGEN RADICAL
CONCENTRATION
($\mu$M)

($\Delta A_{450nm}$)
DIFFERENCE BETWEEN ABSORBANCE OF SAMPLE
AND ABSORBANCE OF Milli Q AQUEOUS SOLUTION OF DBNBS

DETECTION METHOD AND QUANTITATIVE ANALYSIS METHOD FOR HYDROGEN RADICAL

This application is the national phase under 35 U.S.C. § 371 of PCT International Application No. PCT/JP02/05126 which has an International filing date of May 27, 2002, which designated the United States of America.

TECHNICAL FIELD

The present invention relates to a method of detecting hydrogen radicals present in water, particularly in electroreduction water or an aqueous solution, and a method of quantitatively analyzing the concentration of the hydrogen radicals.

BACKGROUND ART

In general, the so-called electroreduction water obtained in a cathode chamber by electrolyzing an electrolytic solution of sodium hydroxide or the like is regarded as having active oxygen eliminating activity and DNA strand break inhibiting activity in the body. This is regarded as resulting from reductiveness of active hydrogen contained in the electroreduction water.

The concentration of hydrogen radicals contained in the electroreduction water or the like influences the active oxygen eliminating activity in the body, and hence establishment of a detection method for hydrogen radicals as well as a quantitative analysis method therefor is required.

The term active hydrogen indicates a hydrogen radical readily causing chemical reaction by a method such as ultraviolet radiation or discharge, and hydrogen formed when acid acts on a metal or arising from a cathode side in electrolysis is also a hydrogen radical having high reactivity. The active hydrogen liberates a metal from alkali metal salt, and readily reduces oxides, sulfides etc. of various metallic elements to metals. Further, the active hydrogen forms a hydride with arsenic, phosphorus, oxygen, halogen, antimony, tin or the like, and forms formaldehydes with carbon monoxide and carbon dioxide. In addition, the active hydrogen causes addition, displacement or hydrogen atom abstraction reaction with various organic compounds, and adds hydrogen to an unsaturated organic compound. Hydrogen radicals, which are relatively stable as such, emit an extremely large quantity of heat and return to general molecules when coming into contact with a metal surface.

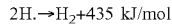

$2H \cdot \rightarrow H_2 + 435$ kJ/mol

The hydrogen radicals are detected through pressure difference when the concentration thereof is high, or through discoloration of tungsten oxide or the like when the quantity thereof is small. However, these methods for detecting hydrogen radicals formed in gas cannot be applied to measurement of hydrogen radicals present in water. Presence of hydrogen radicals in electroreduction water can be proved when the hydrogen radicals can be detected and determined by trapping the same with a water-soluble radical trap agent, and hence study has been progressed in order to establish a detection method and a determination method.

When only a water sample was employed or a water-soluble radical trapping agent of 5,5-dimethyl-1-pyrroline-N-oxide (DMPO) and an aqueous solution sample were reacted with each other for measuring an ESR spectrum with an electron spin resonator (ESR), no spectrum of hydrogen radicals was recognized.

When hydroxide radicals were formed with a Fenton's reagent for confirming decrease of the hydroxide radicals by reducing power of an aqueous solution sample through an ESR spectrum, no clear difference was recognized. Thus, it has been considered difficult to detect hydrogen radicals present in electroreduction water by a method having low detection sensitivity due to low concentration of the hydrogen radicals.

DISCLOSURE OF THE INVENTION

The present invention provides a method of detecting hydrogen radicals present in water or an aqueous solution with high precision and a quantitative analysis method therefor. The inventor has tried to neutralize a large quantity of water samples, react the same with a radical trapping agent of sodium salt of 3,5-dibromo-4-nitrosobenzenesulfonic acid (DBNBS) and thereafter concentrate the same in a rotary evaporator. Consequently, orange coloring was recognized in an electroreduction water sample exhibiting active oxygen eliminating activity. However, no coloring was recognized with respect to ultrapure water (Milli Q water), another mineral water or service water. This was conceivably because DBNBS reacted with active hydrogen present in the electroreduction water to newly form a colored substance. The inventor has considered that hydrogen radicals present in an aqueous solution can be precisely detected through this phenomenon, and developed a detection method and a quantitative analysis method for hydrogen radicals. The present invention is based on the aforementioned recognition, and provides methods of detecting and quantitatively analyzing hydrogen radicals by employing sodium salt of 3,5-dibromo-4-nitrosobenzenesulfonic acid (DBNBS) as a radical trapping agent for electroreduction water or the like.

The present invention is directed to a method of detecting hydrogen radicals present in water or an aqueous solution by adding sodium salt of 3,5-dibromo-4-nitrosobenzenesulfonic acid (DBNBS) to a sample so that the same reacts with the hydrogen radicals thereby forming a DBNBS azo compound and detecting the hydrogen radicals by coloring based on absorption characteristics thereof.

Electroreduction water is preferably employed as the said water or aqueous solution.

The said coloring utilizes such coloring reaction that the sodium salt of 3,5-dibromo-4-nitrosobenzenesulfonic acid (DBNBS) reacts with the hydrogen radicals to form a DBNBS azo compound. The coloring results from an absorption peak at a wavelength of 425 to 450 nm.

The present invention is also directed to a quantitative analysis method for hydrogen radicals present in water or an aqueous solution, consisting of the following steps (1) to (4):

(1) blowing hydrogen gas into a solution of 1,1-diphenyl-2-picrylhydrazyl (hereinafter referred to as DPPH) having absorption in the vicinity of 517 nm at a constant speed in the presence of platinum black for obtaining a graph of correlation between decrease of absorbance in the vicinity of 517 nm and a blowing time of the hydrogen gas (creation of a calibration curve A);

(2) reacting cysteine and DPPH with each other for obtaining a graph of correlation between decrease of absorbance of DPPH in the vicinity of 517 nm and cysteine concentration (creation of a calibration curve B), wherein cysteine can be replaced with a reducing agent such as ascorbic acid;

(3) blowing hydrogen gas into a solution of sodium salt of 3,5-dibromo-4-nitrosobenzenesulfonic acid (DBNBS) at a constant speed in the presence of platinum black for a constant time under the same condition as the said step (1) and thereafter measuring absorbance in the vicinity of 450 nm for obtaining a graph of correlation between the value of the absorbance and the concentration of hydrogen radicals formed per blowing time of the hydrogen gas calculated from the calibration curve A and the calibration curve B (creation of a calibration curve C); and (4) adding sodium salt of 3,5-dibromo-4-nitrosobenzenesulfonic acid (DBNBS) to a sample and measuring absorbance in the vicinity of 450 nm for reading the concentration of the hydrogen radicals from the value of the absorbance through the said calibration curve C.

The water or the aqueous solution is preferably concentrated to have hydrogen radical concentration of 10 to 500 times.

Description is now made on the basis of an embodiment of the present invention.

In the present invention, the method of detecting hydrogen radicals utilizes light absorption characteristics based on reaction shown below. That is, sodium salt of 3,5-dibromo-4-nitrosobenzenesulfonic acid (DBNBS) reacts with hydrogen radicals to form a DBNBS azo compound. The DBNBS azo compound has an absorption peak at a wavelength of 425 to 450 nm, and hence the hydrogen radicals can be detected by coloring thereof.

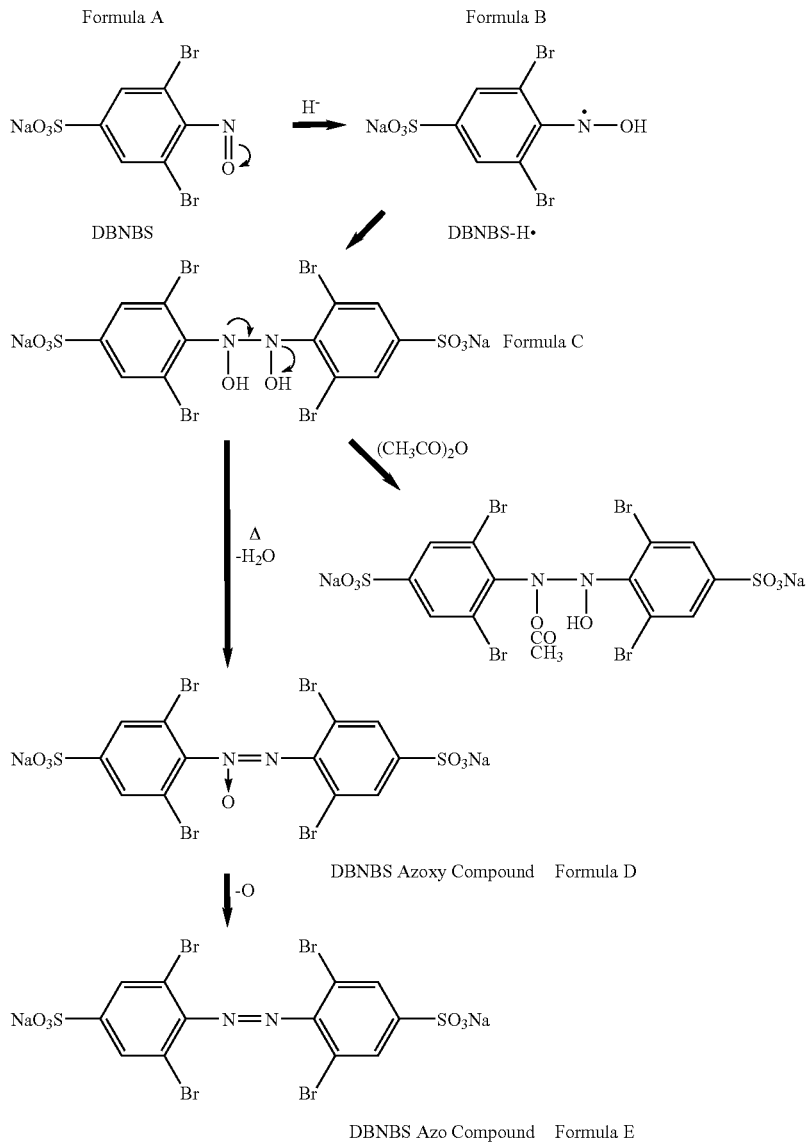

When expressed in reaction formulas, DBNBS (formula A) reacts with hydrogen radicals present in water or an aqueous solution and is converted to DBNBS-H (formula B), and two molecules thereof react with each other to form a dimer (formula C). Thereafter dehydration is performed under heating to form a DBNBS azoxy compound (formula D). One oxygen molecule is taken away to form a stable DBNBS azo compound (formula E). Qualitative analysis of the hydrogen radicals is enabled by detecting absorption at 425 to 450 nm derived from this DBNBS azo compound. While the serial reaction of the above formulas A to E is novel reaction discovered by the inventor for the first time, similar reaction forming azoxybenzene or azobenzene by reduction reaction of nitrobenzene or nitrosobenzene is known (A. Streitwieser, Jr. & C. H. Heathcock: Introduction to Organic Chemistry, pp. 960-965, Macmillan Publishing Co., Inc., New York (1976)). Azoxybenzene and azobenzene are interconvertible to each other by oxidation-reduction reaction.

The hydrogen radicals present in water or an aqueous solution are quantitatively analyzed by the following method:

DPPH is in the form of stable free radicals having specific absorption at a wavelength in the vicinity of 517 nm. DPPH quantitatively reacts with hydrogen radicals, and absorption in the vicinity of 517 nm disappears. On the other hand, granular platinum black having a large surface area converts gaseous hydrogen molecules to hydrogen radicals (atomic hydrogen) and holds the same. Therefore, hydrogen radicals can be readily formed by blowing hydrogen gas into a solution in the presence of platinum black. When hydrogen gas is blown into a DPPH aqueous solution of prescribed concentration in the presence of platinum black under a constant condition, therefore, a calibration curve (A) showing the relation between the blowing time and decrease of the absorption of DPPH at 517 nm can be created.

In order to calculate the concentration of the hydrogen radicals formed per hydrogen gas blowing time, a reducing substance such as cysteine, for example, known as quantitatively reacting and DPPH are reacted with each other for creating a calibration curve (B) showing the cysteine concentration and decrease of the absorbance of DPPH in the vicinity of 517 nm. Assuming that 1 mole of cysteine corresponds to 1 mole of hydrogen radical, the concentration of hydrogen radicals formed per hydrogen gas blowing time is calculated from the calibration curve (A).

On the other hand, DBNBS (formula A) reacts with hydrogen radicals to form the DBNBS azo compound (formula D) through a dihydroxy intermediate (DBNBS-H.) of the formula B and the dimer (formula C) thereof. Specific absorption of the DBNBS azo compound in the vicinity of 450 nm is used for the quantitative analysis. Hydrogen radicals are formed when the hydrogen gas is blown in the presence of platinum black as described above, and hence a calibration curve (C) showing the relation between the absorbance in the vicinity of 450 nm and the concentration of the hydrogen radicals can be obtained through the calibration curves (A) and (B) by obtaining the relation between the absorbance in the vicinity of 450 nm and the hydrogen gas blowing time.

In order to obtain hydrogen radical concentration in a sample, therefore, DBNBS of prescribed concentration is added to a sample solution for reacting DBNBS with hydrogen radicals and forming a DBNBS azo compound, and the absorbance thereof in the vicinity of 450 nm is thereafter measured for measuring the hydrogen radical concentration from the said calibration curve (C).

When electroreduction water is employed as the sample, this electroreduction water is preferably concentrated to 10 to 500 times. For example, 200 μl of DBNBS preservation solution is added to 125 ml of electroreduction water, and the mixture is stirred and thereafter concentrated/exsiccated in a thermostat of 60° C. with a rotary evaporator. The concentrated/exsiccated substance is dissolved in 1 ml of ultrapure water (Milli Q water) and recovered. Then the concentrated/exsiccated substance is heat-retained in the thermostat of 60° C. for about 1 hour, left at rest on ice for 5 minutes and centrifuged at 12,000 rpm, for example, to obtain the supernatant.

BEST MODE FOR CARRYING OUT THE INVENTION

EXAMPLE 1

Detection of Hydrogen Radical Formation by Platinum Black-Hydrogen With DBNBS 1-1 Reagent DBNBS by Labo Tech Co., Ltd., platinum black by Ishifuku Kinzoku Kogyo Kabushiki Kaisha and hydrogen gas by Taiyo Sanso Kabushiki Kaisha were employed. DBNBS was dissolved in ultrapure water (Milli Q water) with concentration of 12.5 mg/ml, preserved at 4° C. and utilized to the fullest within two weeks.

1-2 Formation of Hydrogen Radicals by Platinum Black-Hydrogen

Hydrogen gas is converted to atomic hydrogen on a platinum surface. Therefore, hydrogen gas was blown into 20 ml of a DBNBS solution of 2.5 mg/ml containing 0.01 mg/ml of platinum black at a blowing speed of 45 ml/min. Samples of 200 μl each were recovered after 5, 10, 15, 30, 45 and 60 minutes respectively, centrifuged at 12,000 rpm for 5 minutes and thereafter the supernatants were heat-retained in a thermostat of 60° C. for 1 hour. A control prepared without blowing hydrogen gas was heat-retained at 60° C. for 1 hour.

1-3 Detection of Hydrogen Radicals

The control DBNBS aqueous solution after reaction was calibrated for reducing the absorbance of DBNBS itself to zero, and wavelengths of 350 to 600 nm of the respective DBNBS samples were scanned for obtaining a difference spectrum. This difference spectrum was measured in order to detect that DBNBS was converted to a new substance due to the platinum black-hydrogen treatment. In order to examine whether or not DBNBS specifically reacts with hydrogen radicals resulting from platinum black-hydrogen treatment, samples treated with only platinum black, with only hydrogen gas, with only nitrogen gas and with platinum black-nitrogen gas were also prepared.

Figure 1:
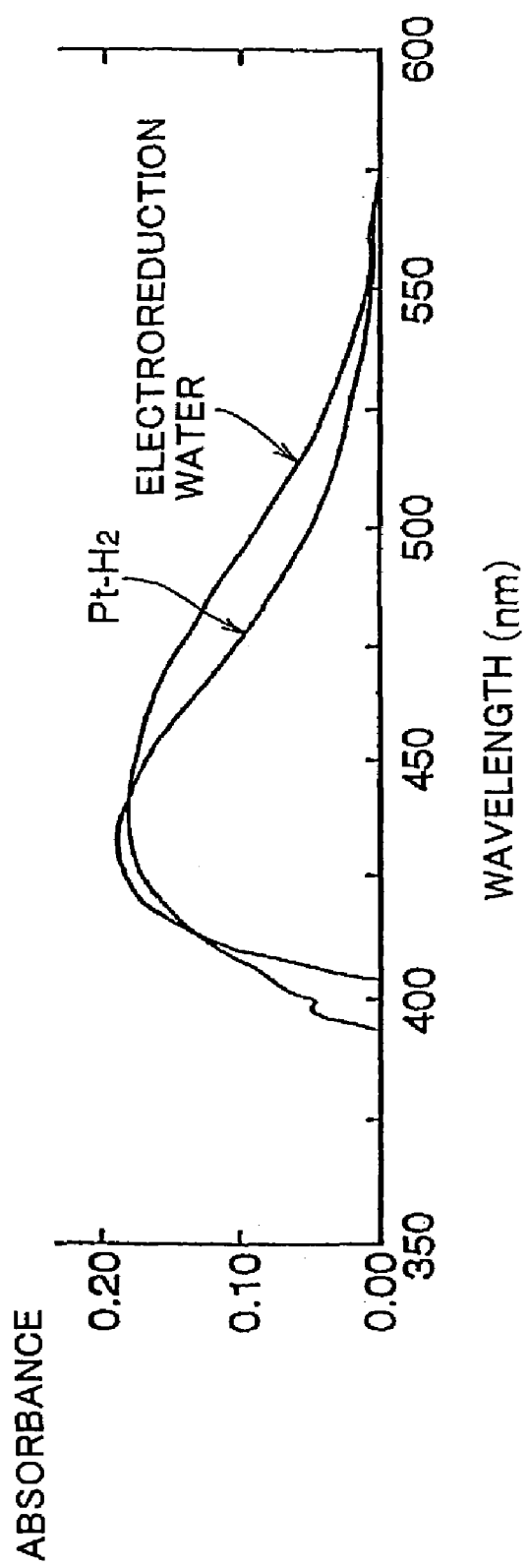
FIG. 1 is a graph showing absorption characteristics of a DBNBS azo compound.
Figure 2:
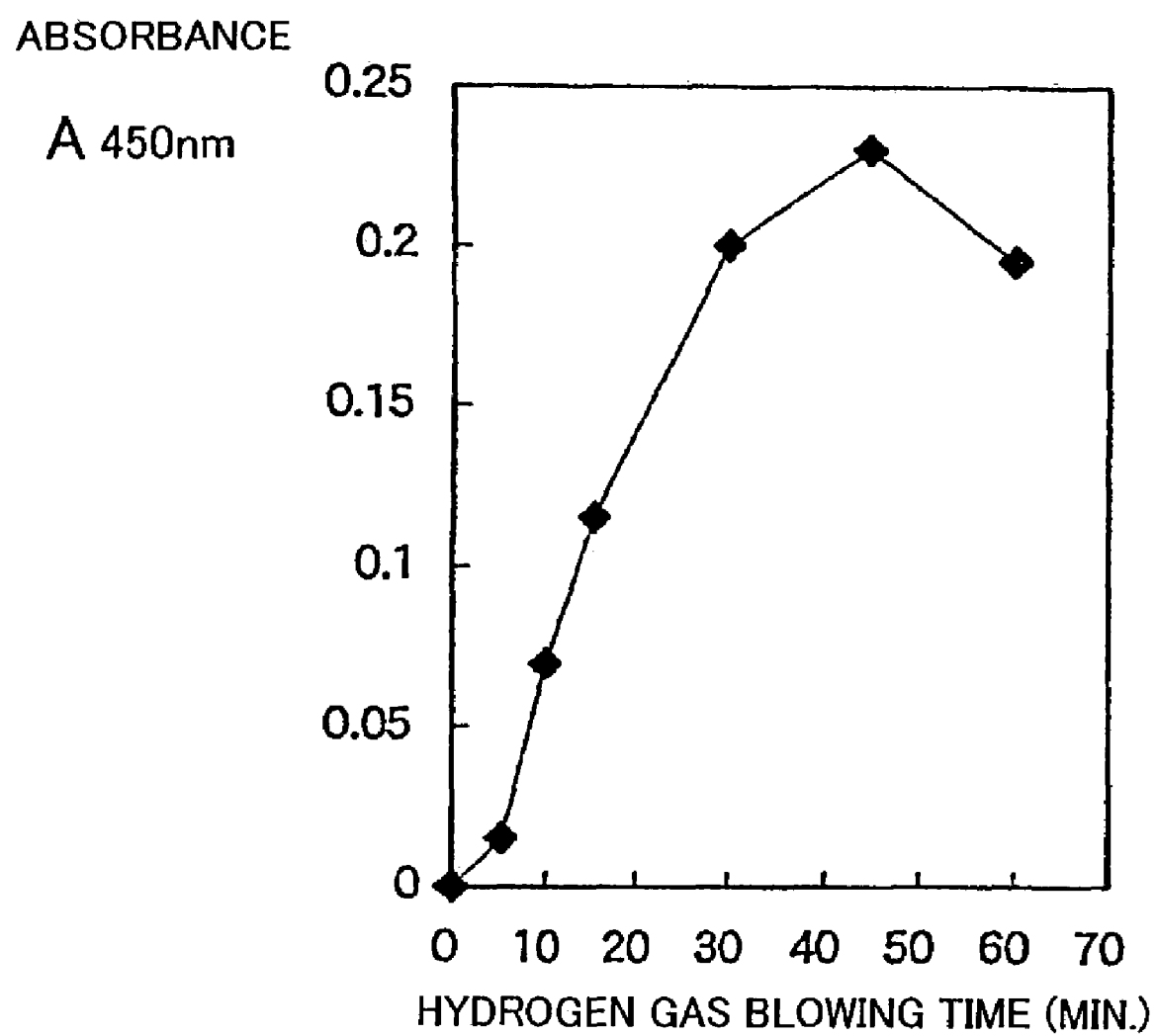
FIG. 2 is a graph showing the relation between a hydrogen gas blowing time and absorbance at 450 nm.

The sample of the DBNBS azo compound obtained by platinum black-hydrogen reaction exhibited a smooth visible absorption spectrum having a peak around 425 nm to 450 nm, as shown in FIG. 1 (Pt—$H_2$). This sample was colored orange. This indicates that DBNBS was converted to the DBNBS azo compound, i.e., a new orange colored substance. The height of the peak was increased depending on the quantity of the blown hydrogen gas, maximized at the blowing time of 45 minutes and thereafter decreased as shown in FIG. 2.

In the samples treated with only platinum black, with only hydrogen gas, with only nitrogen gas and with platinum black-nitrogen gas prepared for examining platinum black-hydrogen reaction specificity, no coloring was recognized and no change was recognized in waveforms in ultraviolet portion absorption either. Absorbance values of absorption spectra of substances obtained by reacting with hydrogen radicals at 450 nm were regarded as hydrogen radical reaction values (AH values).

EXAMPLE 2

Detection of Hydrogen Radicals in Electroreduction Water With DBNBS 2-1 Reagent

The same reagents as those in Example 1 were employed.

2-2 Electroreduction Water 0.01% NaCl water was electrolytically reduced by an electroreduction water device TI-8000 by Nihon Trim Co., Ltd. at a level 4 (5A), for obtaining electroreduction water on a cathode side.

2-3 Detection of Hydrogen Radicals

200 μl of a DBNBS preservation solution was added to 125 ml of electroreduction water, and the mixture was stirred and thereafter concentrated/exsiccated in a thermostat of 60° C. with a rotary evaporator. The concentrated/exsiccated substance was dissolved in 1 ml of ultrapure water (Milli Q water) and recovered. Then, the concentrated/exsiccated substance was heat-retained in the thermostat of 60° C. for 1 hour, left at rest on ice for 5 minutes and centrifuged at 12,000 rpm, to obtain the supernatant. A DBNBS sample similarly prepared with the aforementioned ultrapure water as a control was calibrated and wavelengths of 350 to 600 nm of the DBNBS sample were scanned for obtaining a difference spectrum.

A spectrum similar to the absorption spectrum obtained in Example 1 was recognized in the electroreduction water (FIG. 1: electroreduction water), and it was confirmed that hydrogen radicals were present in the electroreduction water.

EXAMPLE 3

Relation between Concentration of Electroreduction Water and Hydrogen Radical Reaction Value and Relation Between Electrolytic Strength and Hydrogen Radical Reaction Value Whether or not there is correlation between concentration of electroreduction water and a hydrogen radical quantity was tested. The electroreduction water was diluted with ultrapure water (Milli Q water), for measuring hydrogen radical reaction values of samples respectively. In order to examine the relation between electrolytic strength and the hydrogen radical reaction values, water samples having NaCl concentration values of 0.0001% to 0.01% were prepared for measuring active hydrogen reaction of water samples prepared by electrolytically reducing the respective samples. The water samples were electrolytically reduced with the electroreduction water apparatus TI-8000 by Nihon Trim Co., Ltd. At a level 4 (5A), for obtaining reduction water samples on cathode sides.

Figure 3:
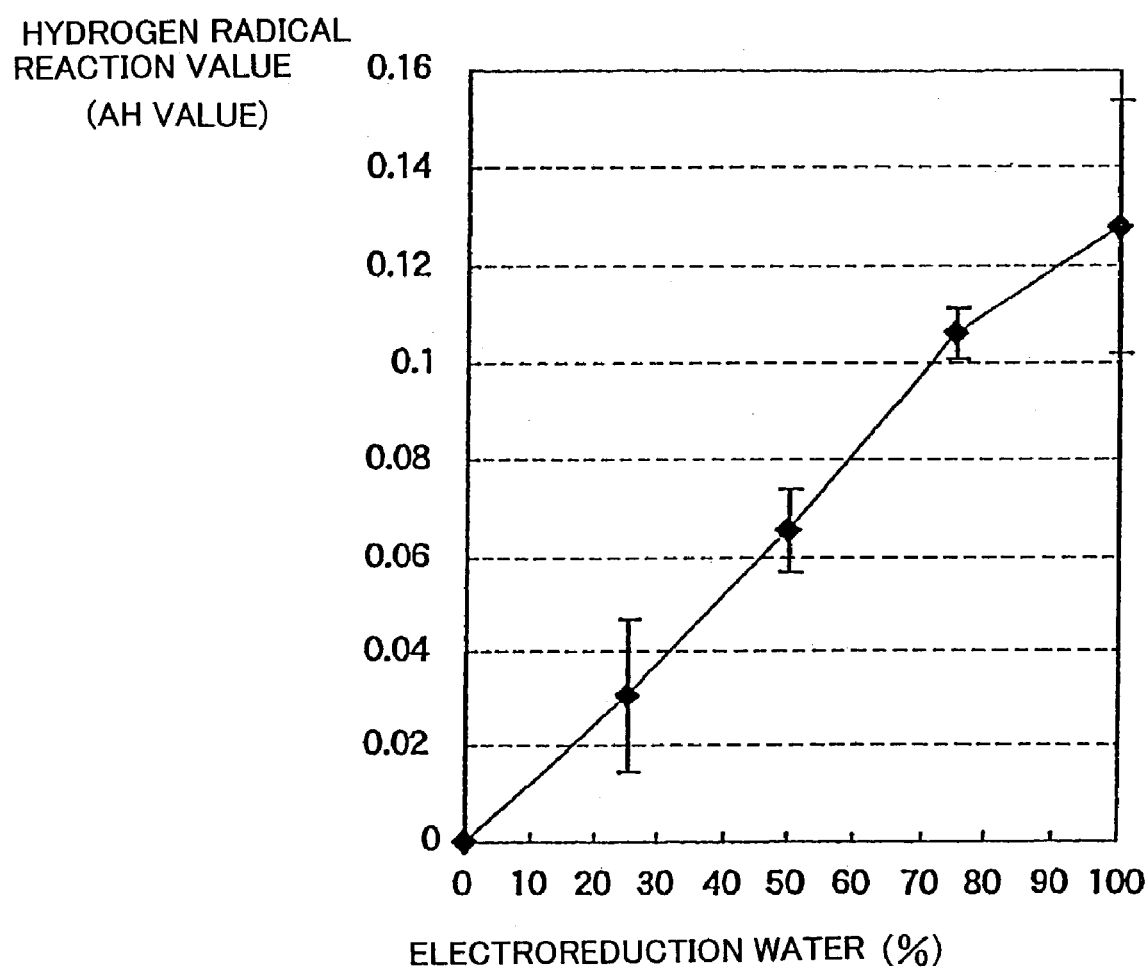
FIG. 3 is a graph showing the relation between electroreduction water and hydrogen radical reaction values.
Figure 4:
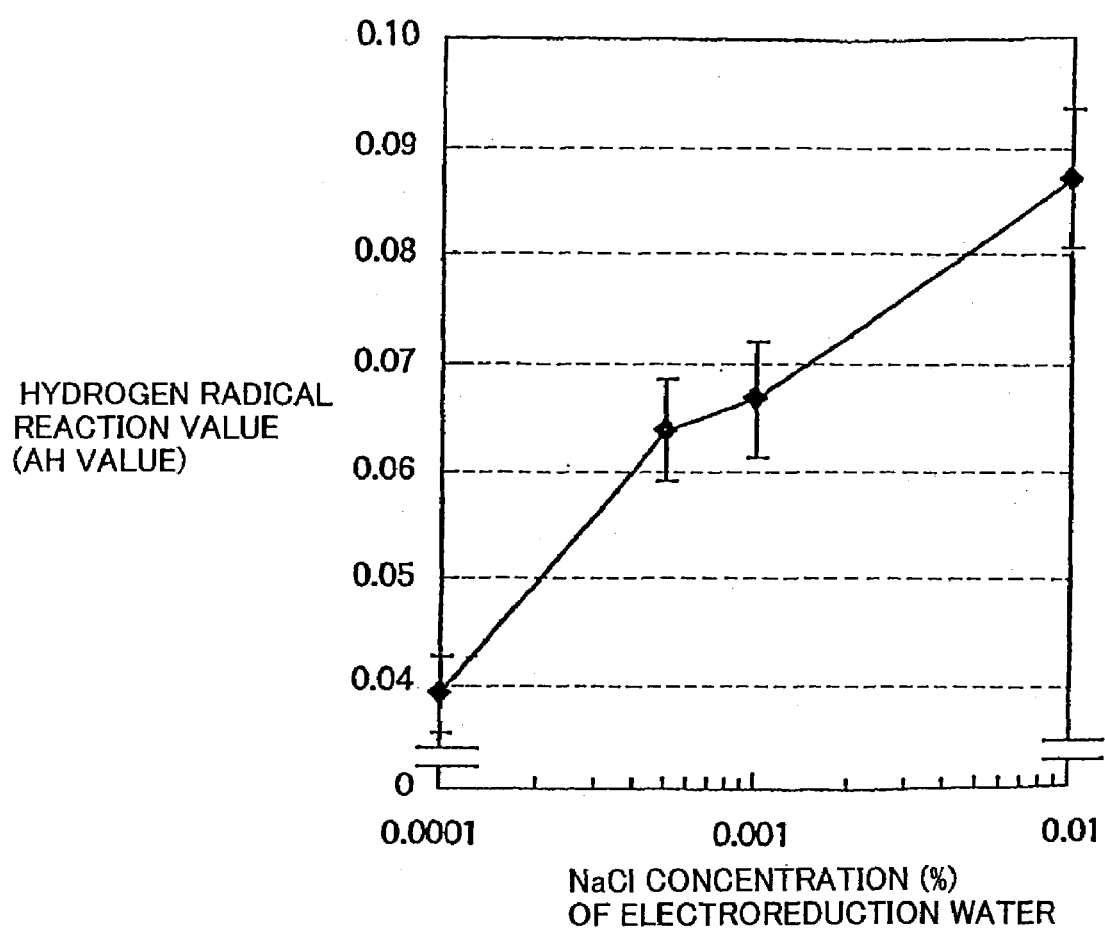
FIG. 4 is a graph showing the relation between sodium chloride concentration and hydrogen radical reaction values.

When water samples containing 25, 50, 75 and 100 volume % of the electroreduction water samples were prepared by dilution for measuring hydrogen radical reaction values, the hydrogen radical reaction values were increased along with the concentration of the electroreduction water as shown in FIG. 3, and hence it has been clarified that this system of measurement has quantitativeness also in the samples of the electroreduction water. In electroreduction water obtained by varying salt concentration (NaCl concentration) of an aqueous solution for creating an aqueous solution having different electrolytic strength when obtaining electroreduction water by electrolysis, the hydrogen radical reaction value was also increased along with the electrolytic strength (NaCl concentration) as shown in FIG. 4. This indicates that a large quantity of hydrogen radicals are also formed when increasing the electrolytic strength.

EXAMPLE 4

Analysis of Reaction Process of Hydrogen Radicals and DBNBS 4-1 Sample

DBNBS by Labo Tech Co., Ltd., type M platinum black powder by Ishifuku Kinzoku Kogyo Kabushiki Kaisha and hydrogen gas by Taiyo Sanso Kabushiki Kaisha were employed respectively.

4-2 Reaction of DBNBS

A sample prepared by blowing hydrogen gas into 20 ml of a DBNBS solution of 2.5 mg/ml containing 0.01 mg/ml of platinum black at a blowing speed of 45 ml/min. for 1 hour with no heat treatment and a sample heat-treated at 60° C. for 1 hour and cooled with ice for stopping reaction were employed as analytical samples.

4-3 Adjustment of Analytical Sample (1) High Performance Liquid Chromatogram (HPLC) Analytical Sample The analytical samples were filtrated through filters of 0.45 μm respectively, and parts of 2000 μl thereof were employed.

(2) Analytical Sample in NMR and TOF-MASS Analysis

An unheated reaction intermediate separated from the HPLC was acetylated with acetic anhydride (by Wako Pure Chemical Industries, Ltd.) and stabilized while an azo compound separated by heat treatment was HPLC-isolated again for completing the degree of separation.

(3) Analytical Sample in Trace Element Analysis

An unheated reaction intermediate separated from the HPLC was employed and an azo compound separated by heat treatment was prepared similarly to that in NMR and TOF-MASS analysis.

4-4 Apparatus Measurement Condition (1) HPLC was prepared from Waters600E by Waters with a mobile phase of Milli-Q Water at a flow velocity of 5 ml/min. by a quantity of injection of 2000 μl sampled by an auto sampler Waters717 while employing a column Nova-Pak C18 of 19 by 300 mm by Waters. A photodiode array detector Waters996 by Waters was employed as a detector for capturing data in a wave range of 200 to 600 nm at intervals of 1.2 nm. A spectral chromatogram was analyzed with a Compaq V700 personal computer through a program created by Millennium 32 (Waters).

(2) A TOF-MASS analyzer Voyager (perceptive by Applied Biosystems Japan Ltd.) was employed. Voyager is a laser ionization time-of-flight mass spectrometer having an acceleration voltage of 20 kV. The acceleration voltage was set to 20 kV for making analysis in a linear flight mode. A matrix was prepared by dissolving 1.3 mg of 2-(4-hydroxyphenylazo)-benzoic acid (HABA) (by Aldrich Chemical Co., Ltd.) in 1 ml of 50:50 water acetonitrile. A sample slide was coated with 0.5 μl of the sample and naturally dried followed by addition of the same quantity of a matrix solution, while the sample was naturally dried again and introduced into an ion source.

(3) An NMR (JEOL JNM-GSX400 NMR System Spectrometer) of 400 MHz was Employed for Performing 1H-NMR Measurement. Dimethylsulfoxide (DMSO) (by Wako Pure Chemical Industries, Ltd.) and deuterium oxide ($D_2O$) (by Aldrich Chemical Co., Ltd.) were employed as solvents.

4-5 Analytical Result (A) Result of High Performance Liquid Chromatogram (HPLC) Measurement (i) Analytical Sample (1)

Figure 5:
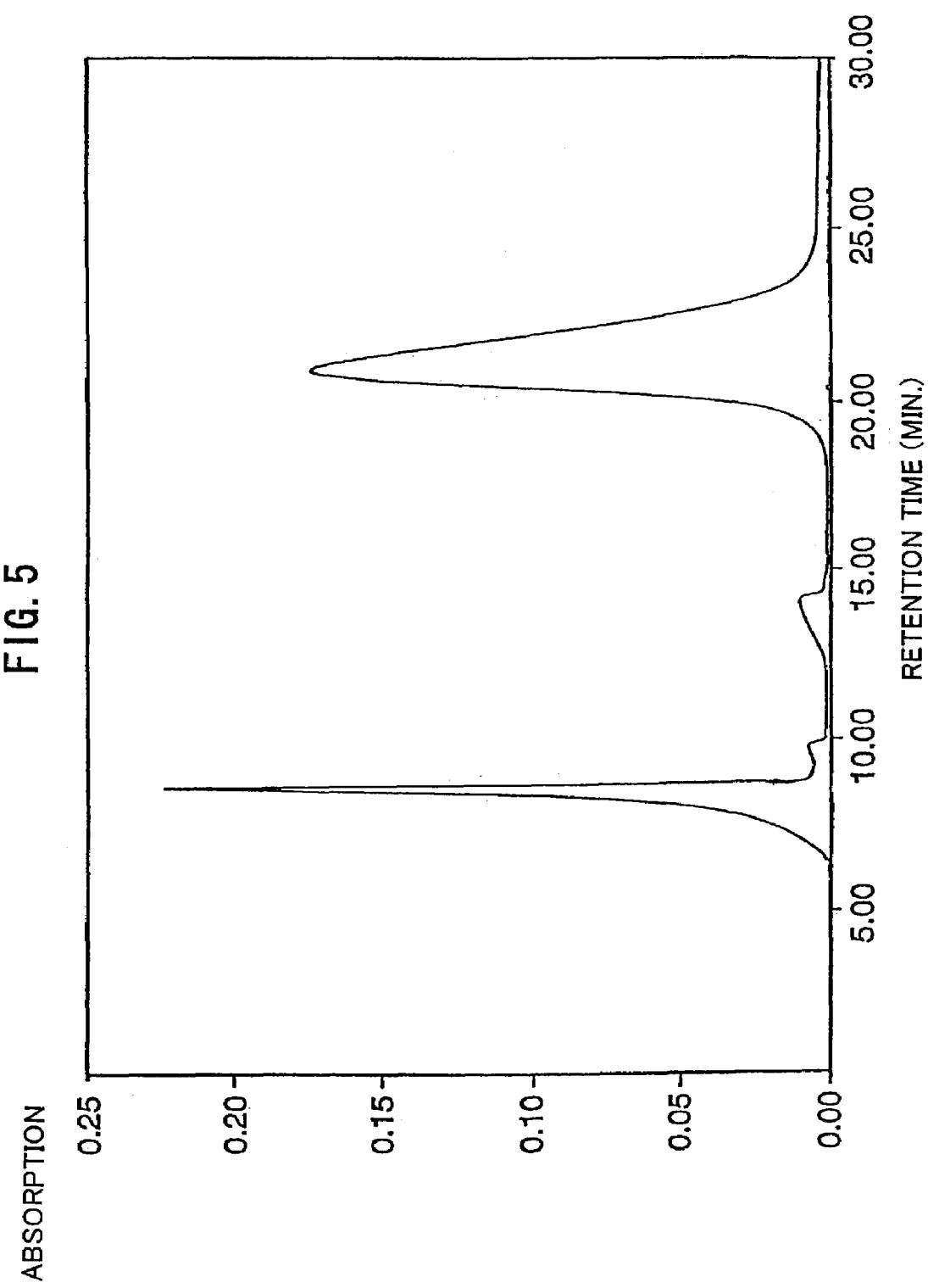
FIG. 5 is a chart showing a result of HPLC measurement of a DBNBS unheated reactant.
Figure 6:
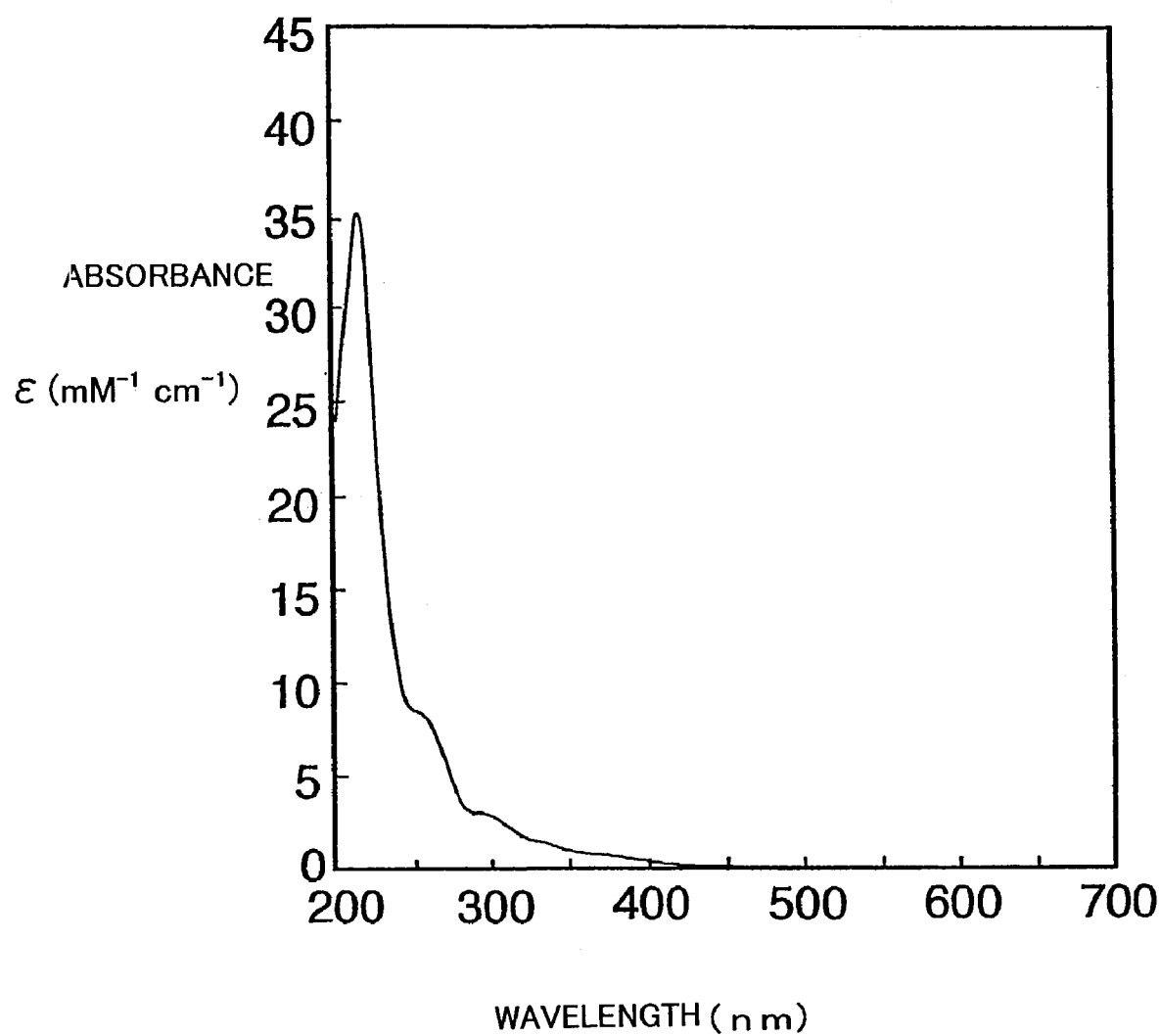
FIG. 6 is a chart showing an ultraviolet visible absorption spectrum of the DBNBS unheated reactant.

Hydrogen gas was blown into 20 ml of a DBNBS solution of 2.5 mg/ml containing 0.01 mg/ml of platinum at a blowing speed of 45 ml/min. and this solution was filtrated through a filter of 0.45 μm so that 2000 μl of this unheated sample was measured with an HPLC provided with a photodiode array detector. FIG. 5 shows the result of the measurement. The peak of the unheated DBNBS reactant recognized at the retention time of about 9.0 minutes in FIG. 5 exhibited an absorption peak at 220 nm while exhibiting no absorption at 450 nm as understood from an ultraviolet visible absorption spectrum shown in FIG. 6. This was estimated as corresponding to the dimer expressed in the formula C.

(ii) Analytical Sample (2)

Figure 7:
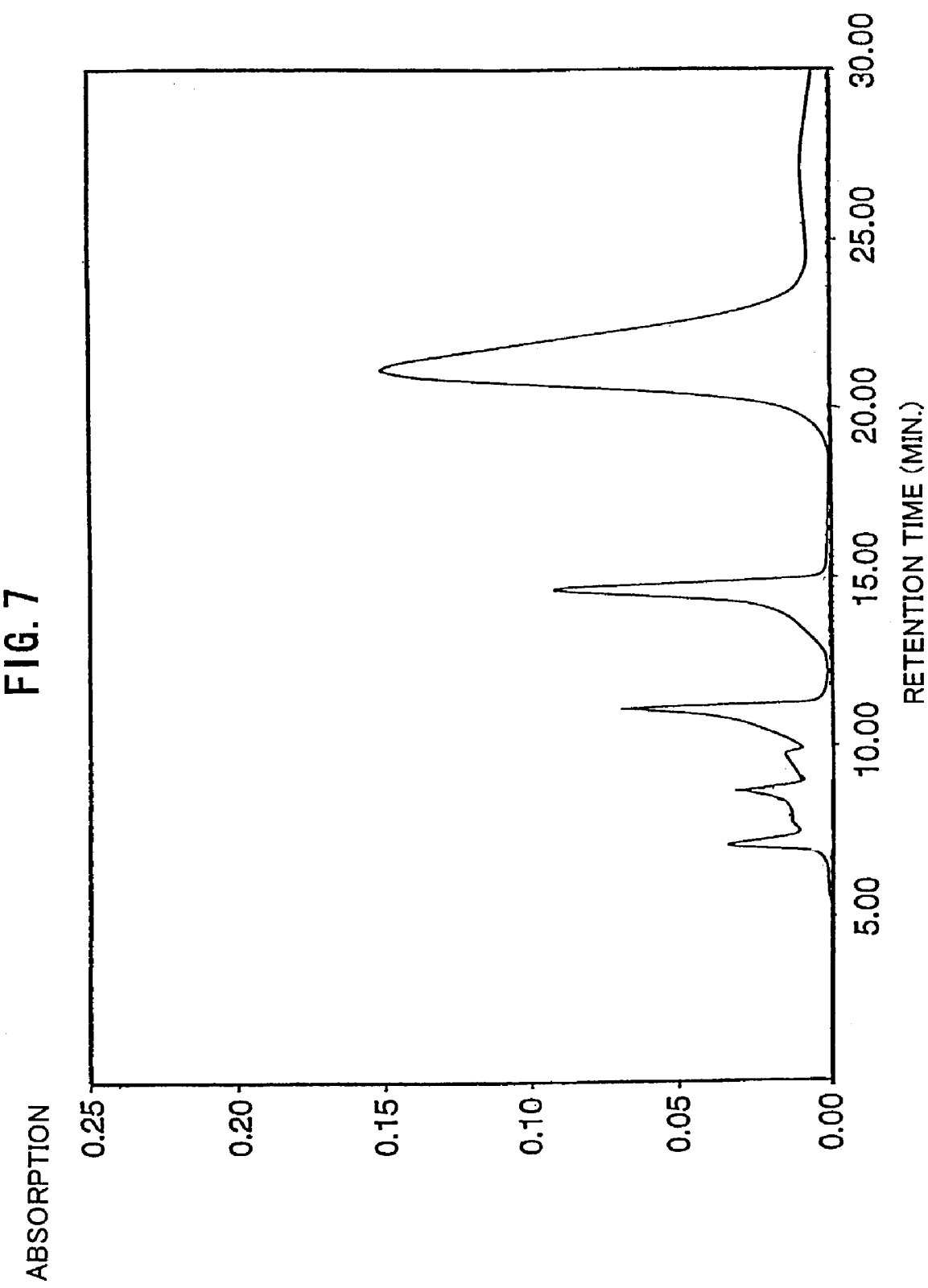
FIG. 7 is a chart showing a result of HPLC measurement of a DBNBS heated reactant.
Figure 8:
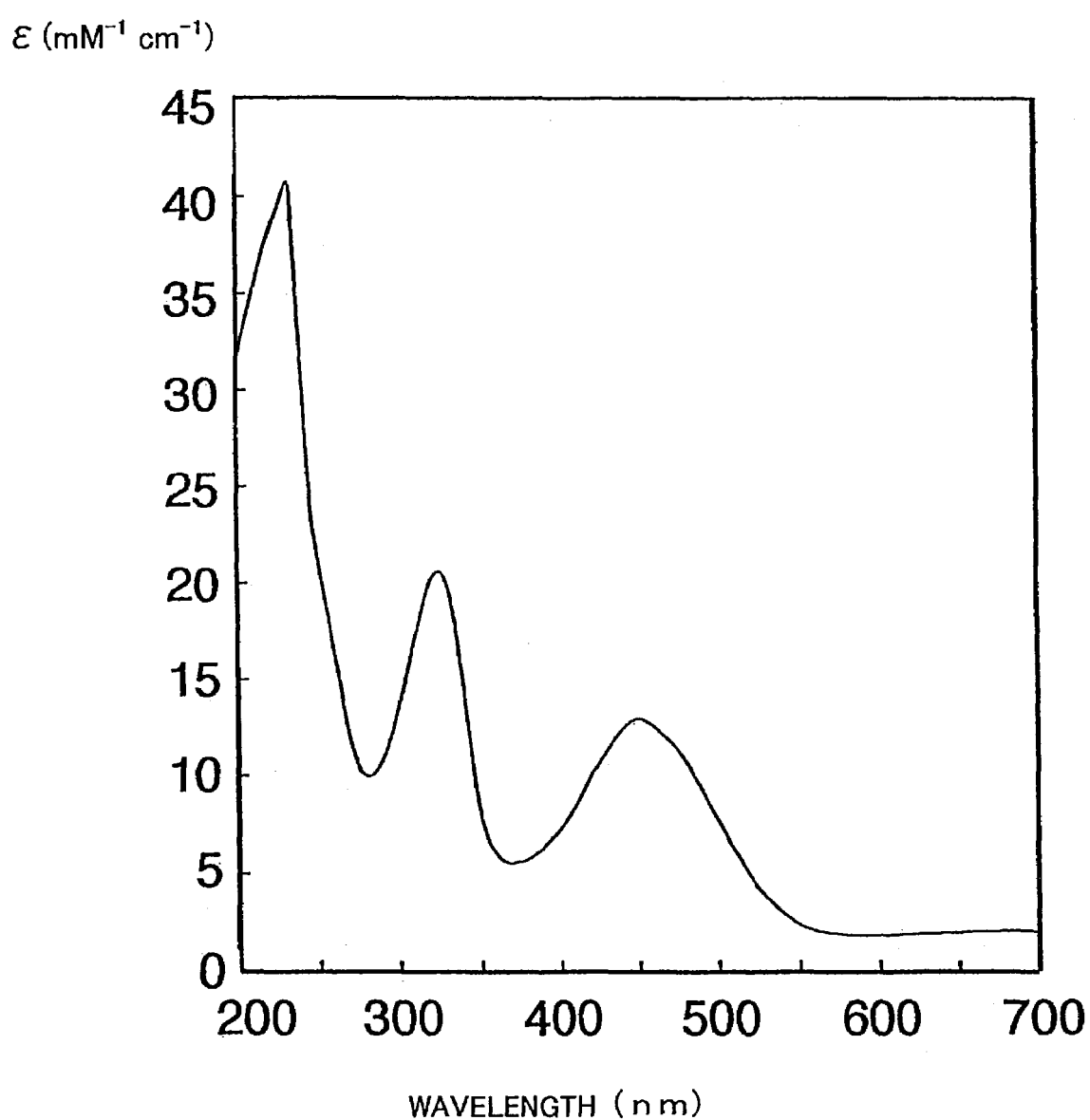
FIG. 8 is a chart showing an ultraviolet visible absorption spectrum of the DBNBS heated reactant.

Hydrogen gas was blown into 20 ml of a DBNBS solution of 2.5 mg/ml containing 0.01 mg/ml of platinum at a ventilation speed of 45 ml/min. and the solution was heat-treated at 60° C. for 1 hour, cooled with ice for stopping reaction and filtrated through a filter of 0.45 μm so that 200 μl of this heated sample was measured with an HPLC provided with a photodiode array detector. FIG. 7 shows the result of the measurement. As to the peak of the heated DBNBS reactant recognized at the retention time of 8.5 minutes in FIG. 7, absorption peaks were recognized at 320 nm and 450 nm to exhibit an ultraviolet absorption spectrum similar to known azobenzene, as understood from the ultraviolet visible absorption spectrum shown in FIG. 8. This corresponds to the DBNBS azo compound expressed in the formula E.

(B) Result of Measurement of Mass Spectrum (MALDI-TOF-MS)

(i) Analytical Sample (1)

The unheated DBNBS reactant having absorption at 280 nm obtained in the aforementioned HPLC measurement was measured through a mass spectrum (MALDI-TOF-MS).

Figure 9:
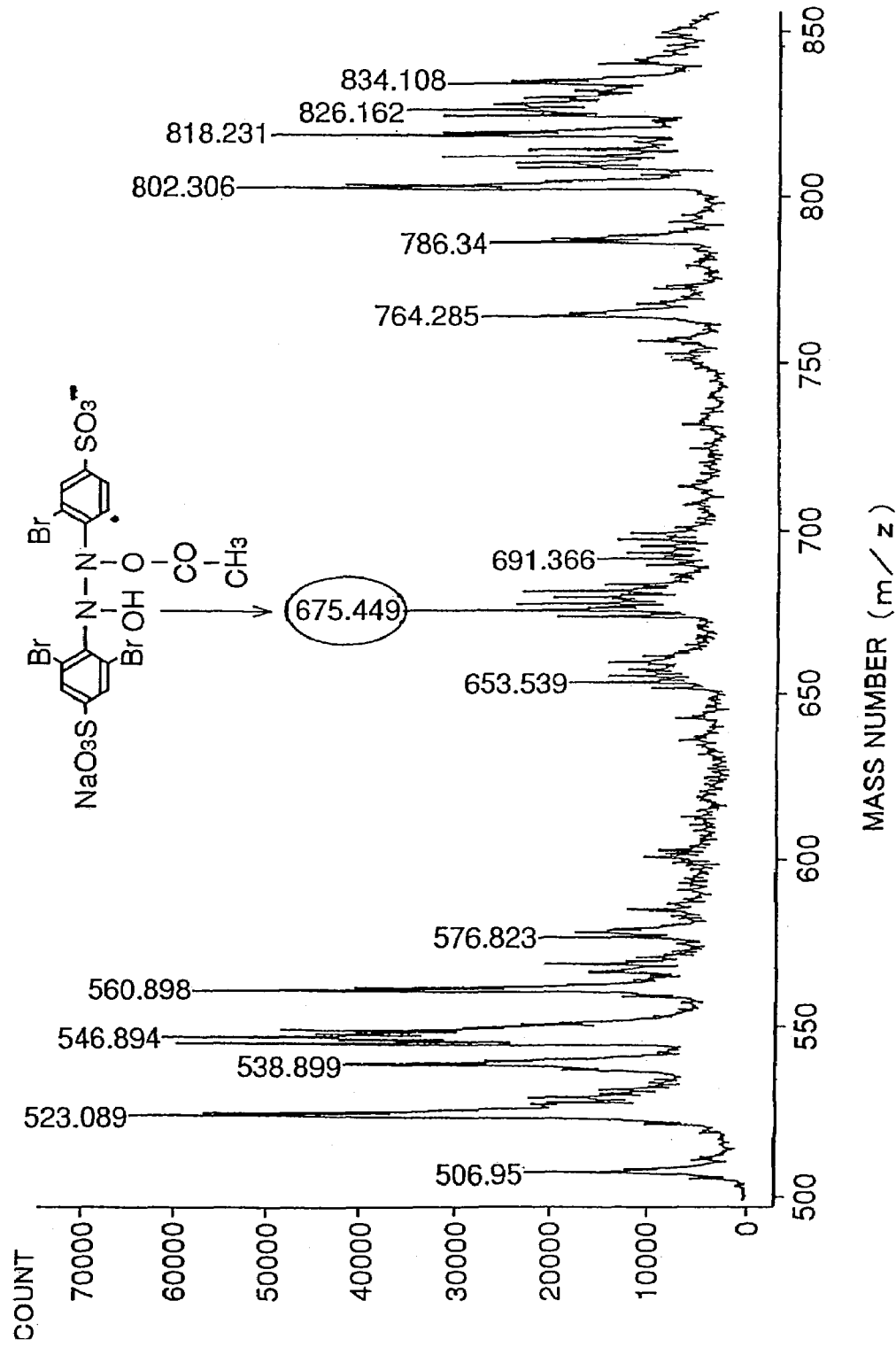
FIG. 9 is a mass spectrum measurement chart of the DBNBS unheated reactant.

The mass spectrum of the acetylated unheated DBNBS reactant having absorption at 280 nm exhibited an ion peak at m/z 675.449 as shown in FIG. 9, and this coincided with such a substance that one Br molecule and one Na molecule are desorbed from the intermediate (formula C) and one hydroxyl group of the intermediate of the formula C is acetylated.

(ii) Analytical Sample (2)

The heated DBNBS reactant having absorption at 450 nm obtained in the aforementioned HPLC measurement was measured through a mass spectrum (MALDI-TOF-MS).

Figure 10:
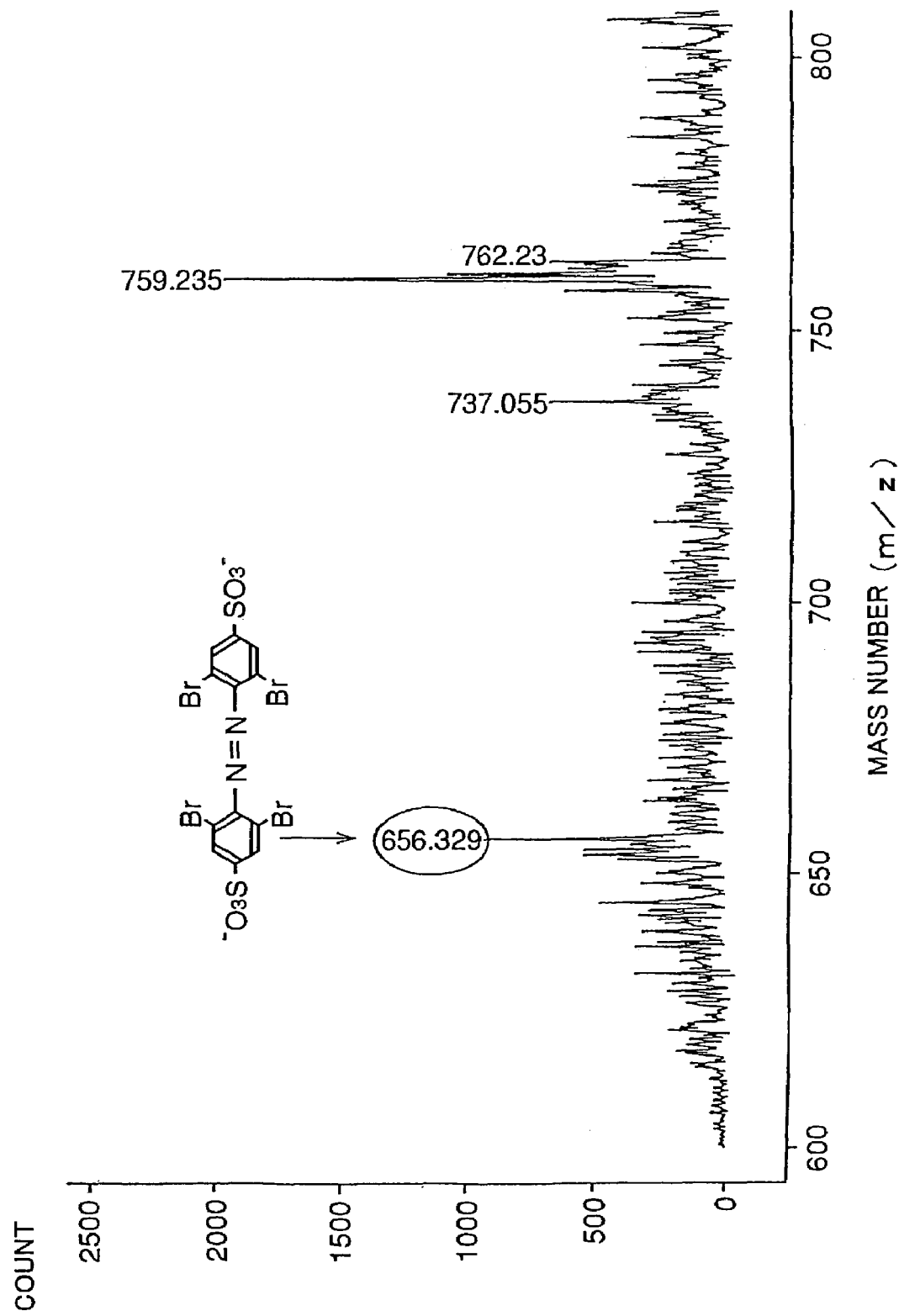
FIG. 10 is a mass spectrum measurement chart of the DBNBS heated reactant.

The mass spectrum of the heated DBNBS reactant having absorption at 450 nm exhibited an ion peak at m/z 656.329 as shown in FIG. 10, and this corresponded to the DBNBS azo compound (formula E) from which two Na molecules were desorbed.

(C) Result of NMR Measurement (i) Analytical Sample (1)

Figure 11:
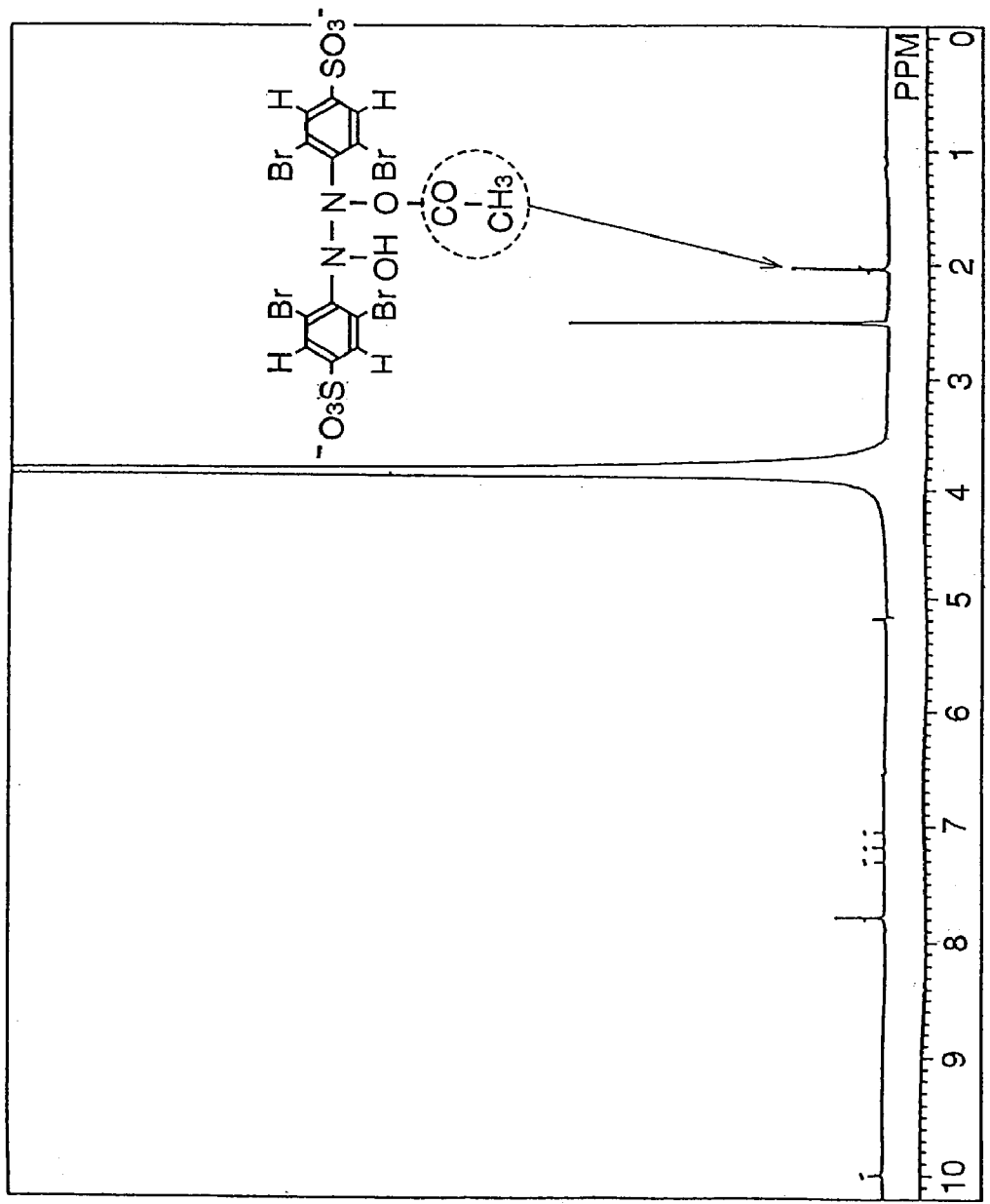
FIG. 11 is an NMR spectrum measurement chart of the DBNBS unheated reactant.

FIG. 11 shows a result obtained by measuring the unheated DBNBS reactant having absorption at 280 nm obtained in the aforementioned HPLC measurement with a 1H-NMR. FIG. 11 shows the spectrum of the acetylated unheated DBNBS reactant having absorption at 280 nm. A control prepared by collecting acetic anhydride employed for acetylation similarly by HPLC isolation was measured. While methyl groups of the control of acetic anhydride exhibited a signal at 2.5 ppm, presence of methyl groups shown at a chemical shift of 2.0 ppm indicates that hydroxyl groups of the unheated DBNBS reactant and acetic anhydride caused direct reaction.

(ii) Analytical Sample (2)

Figure 12:
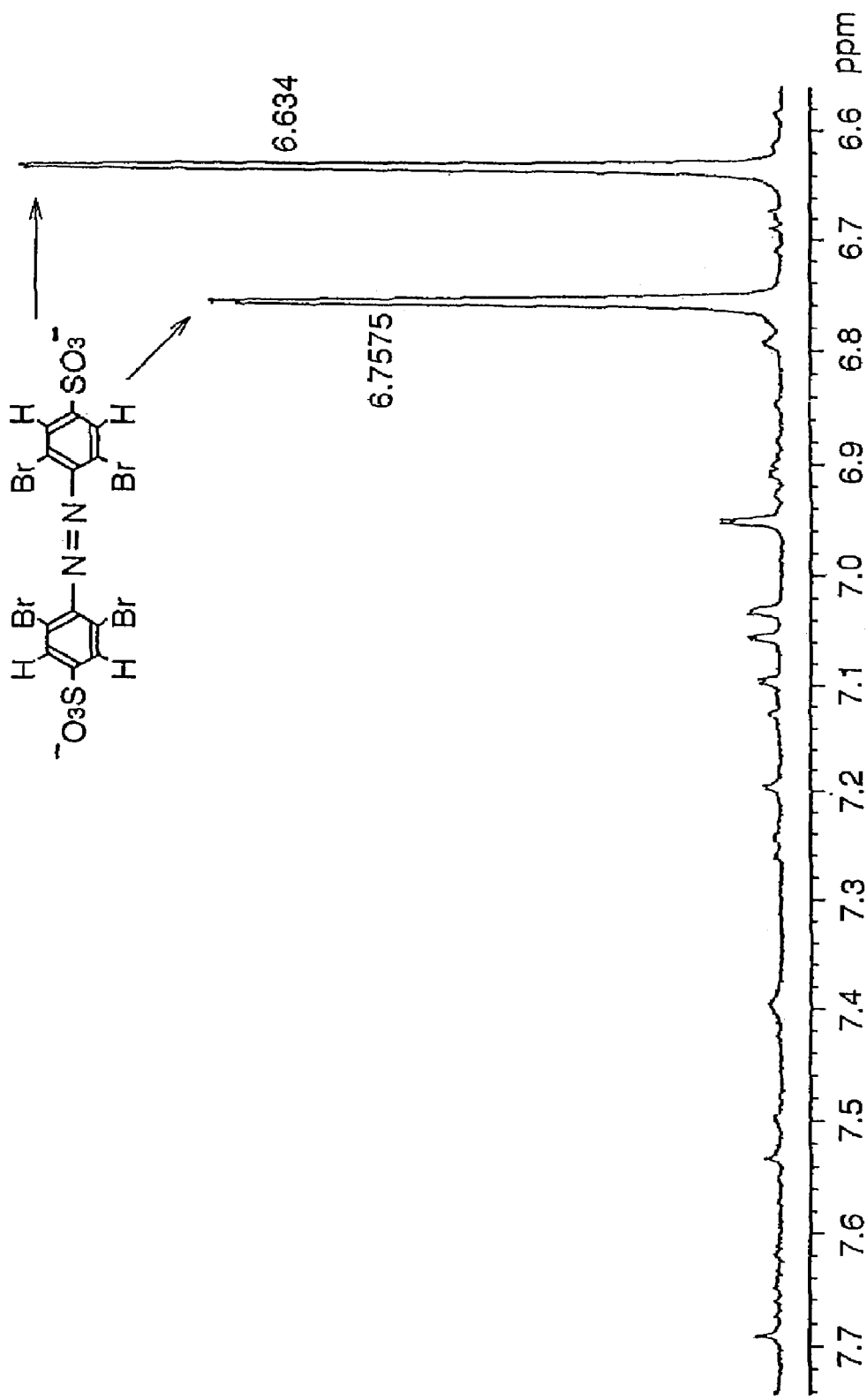
FIG. 12 is an NMR spectrum measurement chart of the DBNBS heated reactant.

FIG. 12 shows a result obtained by measuring the heated DBNBS reactant having absorption at 450 nm obtained in the aforementioned HPLC measurement with a 1H-NMR. While DBNBS exhibited a single signal at 8.0 ppm, proton and chemical shifts of the heated DBNBS reactant having absorption at 450 nm are at 6.6 to 6.8 ppm, and signals at 6.7575 ppm and 6.634 ppm are further split into right and left single symmetric signals. This indicates that protons on meta positions were rendered asymmetric and coupling took place between the protons following formation of azo groups.

(D) Result of Trace Element Analysis (i) Analytical Sample (1)

The unheated DBNBS reactant having the absorption peak at 220 nm obtained in the aforementioned HPLC measurement was subjected to trace element analysis. The carbon content was 19.93% (calculated value: 19.35%), the hydrogen content was 1.61% (calculated value: 1.61%) and the nitrogen content was 3.76% (calculated value: 3.76%). This coincides with such a substance that two Na molecules are desorbed from a trihydrate of the intermediate.

(ii) Analytical Sample (2)

The heated DBNBS reactant having absorption at 450 nm obtained in the aforementioned HPLC measurement was subjected to trace element analysis.

The carbon content was 21.53% (calculated value: 21.43%), the hydrogen content was 1.73% (calculated value: 1.79%) and the nitrogen content was 3.84% (calculated value: 4.17%). This coincides with such a substance that one Br molecule and one Na molecule are desorbed from a tetrahydrate of the DBNBS azo compound.

EXAMPLE 5

Quantitative Analysis of Hydrogen Radicals 5-1 Creation of Calibration Curve A (Relation between, 1-Diphenl-2-Picrylhydrazyl (DPPH) and Hydrogen Gas Blowing Time)

Figure 13:
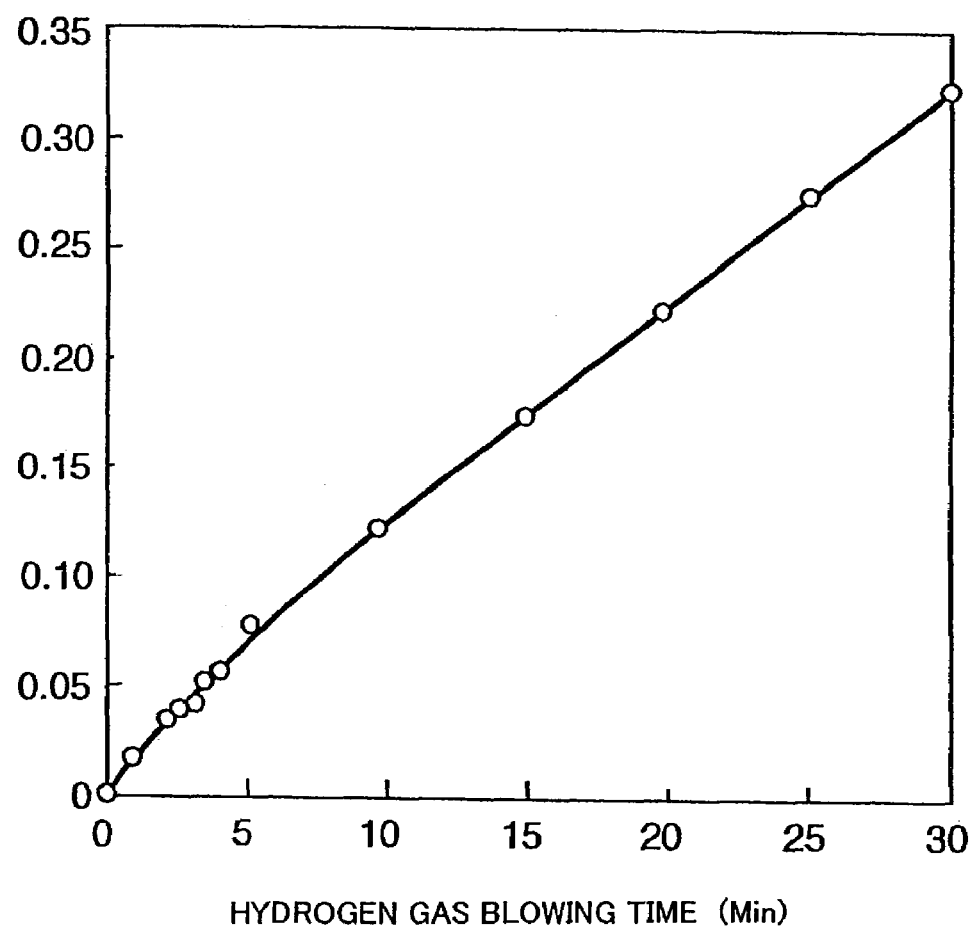
FIG. 13 is a graph showing a calibration curve A.

1 ml of a solution of ethanol and 0.5 mM of DPPH and 0.05 ml of 1.0 mg/ml of platinum black-acetic acid buffer solution were added to 1.96 ml of 0.1 M acetic acid buffer solution (pH 5.5) so that the total weight was 5 ml, and hydrogen gas was blown into the mixture at a speed of 45 ml/min. for collecting a sample of 200 μl every constant time and measuring absorbance at 517 nm indicating specific absorption of DPPH, thereby obtaining a graph (calibration curve A) of FIG. 13 indicating the relation between decrease of the absorbance and the blowing time.

Figure 14:
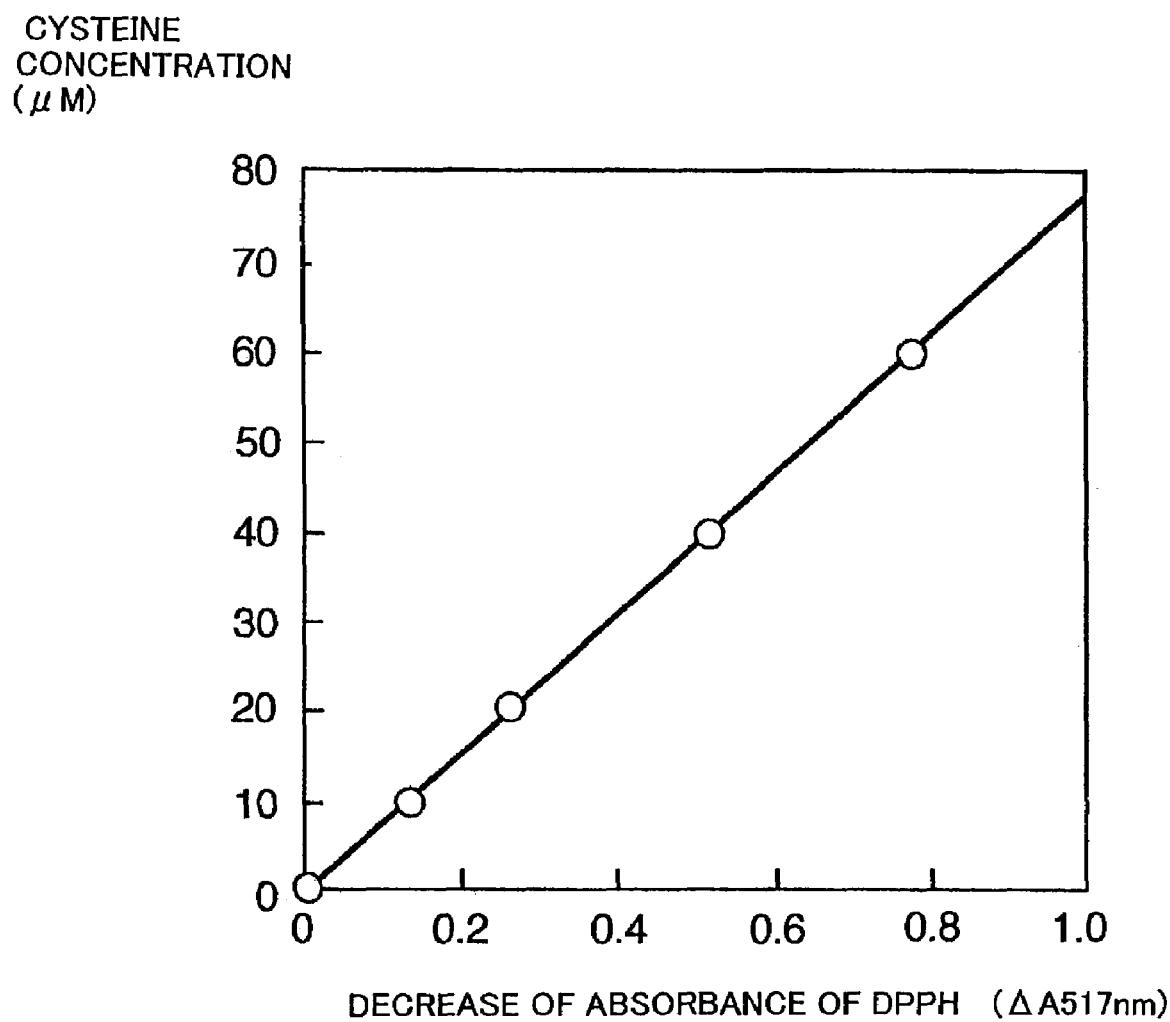
FIG. 14 is a graph showing a calibration curve B.

5-2 Creation of Calibration Curve B 0 to 100 μM of cysteine and DPPH were reacted with each other for obtaining a graph of correlation between decrease of absorbance of DPPH in the vicinity of 517 nm and the cysteine concentration. FIG. 14 shows the graph of a calibration curve B.

5-3 Creation of Calibration Curve C (Relation between Absorbance of Sodium Salt Azo Compound (DBNBS Azo Compound) of 3,5-Dibromo-4-Nitrosobenzenesulfonic Acid and Hydrogen Radical Concentration)

Figure 15:
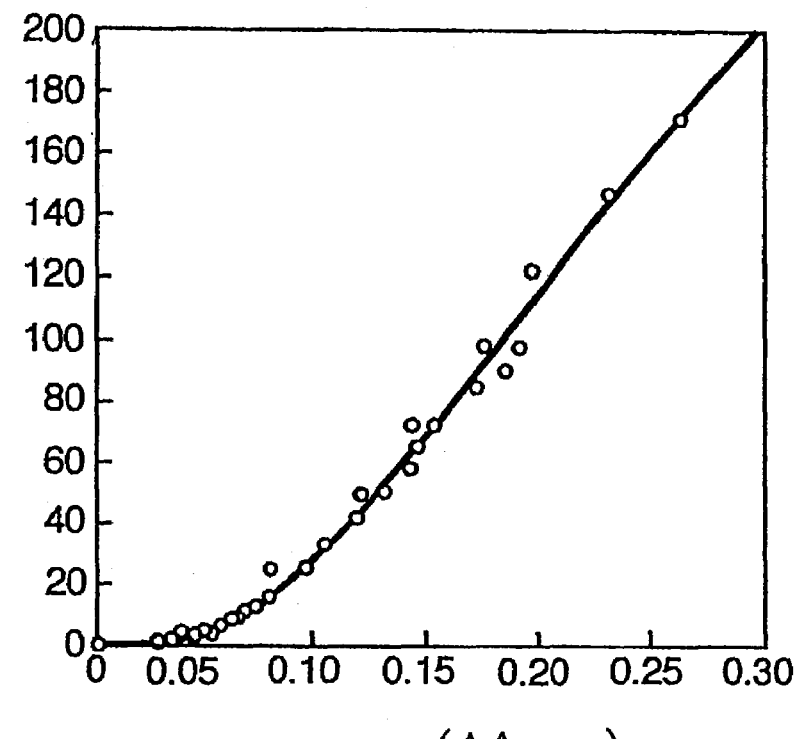
FIG. 15 is a graph showing a calibration curve C.

Hydrogen gas was blown into 5 ml of a DBNBS solution of 2.5 mg/ml containing 0.01 mg/ml of platinum at a speed of 45 ml/min. for collecting a sample of 200 μl every constant time while reacting DBNBS and hydrogen radicals with each other, warming the sample at 60° C. for 1 hour and thereafter measuring absorbance at 450 nm indicating specific absorption of a DBNBS azo compound, i.e., the reaction product of DBNBS and the hydrogen radicals, thereby creating a calibration curve C shown in FIG. 15.

5-4 Measurement of Hydrogen Radical Concentration in Sample (1) Sample Preparation Electroreduction water was prepared to pH 7.0, for preparing samples of levels 1 to 4 according to preparation conditions therefor. The electroreduction water was obtained in a cathode chamber by introducing aqueous solutions containing NaOH into the said cathode chamber and an anode chamber isolated from each other by a diaphragm respectively, making energization between the cathode and the anode and electrolyzing the said NaOH aqueous solutions. Table 1 shows oxidation-reduction potentials (ORP) and pH values of these samples. Ultrapure water (Milli Q water) was employed as a control sample.

200 μl of a DBNBS stock solution (12.5 mg/ml) was added to each of 125 ml of Milli Q water and the electroreduction water samples of levels 1 to 4, and the mixture was vacuum-concentrated to 125 times. The inner wall of a Kjeldahl flask was washed with 1 ml of Milli Q water after concentration, and the solution was left at rest for a while and recovered. The recovered solution was heated in a 60° C. hot water bath (screened), and thereafter cooled in ice for stopping reaction. The solution was centrifuged at a rotational speed of 12000 rpm for 5 minutes, for sampling the supernatant.

(2) Measurement of Absorbance

Absorbance values of the aforementioned samples were measured at a frequency of 450 nm. The measurement was made on three samples as to each level, for obtaining the average of the measured values. Table 1 shows results of measurement of the absorbance. As a result of the analysis with an HPLC, it has been identified from positions of elution and ultraviolet visible absorption spectra that each colored substance resulting from reaction between the electroreduction water and DBNBS was identical to the DBNBS azo compound formed by blowing hydrogen gas in the presence of platinum black.

(3) Measurement of Hydrogen Radical Concentration

Average absorbance of 0.0358 of the Milli Q aqueous solution of DBNBS employed as the control, obtained at 450 nm was subtracted from the absorbance of the sample of each level, for obtaining hydrogen radical concentration from the value of absorbance of the difference through the calibration curve (C). The hydrogen radical concentration values of the electroreduction water concentrated to 125 times were in the range of 7 to 34 μM (μmol/l) at the levels 1 to 4.

TABLE 1

|  | Mill:Q | Level 1 | Level 2 | Level 3 | Level 4 |
| --- | --- | --- | --- | --- | --- |
| pH | — | 8.52 | 9.27 | 9.84 | 10 |
| Oxidation-Reduction Potential ORP(mV) | — | 56 | 38 | 4 | 1 |
| Absorbance (average) (450 nm) | 0.0358 | 0.0927 | 0.1037 | 0.0975 | 0.1462 |
| Difference in Absorbance (with reference to Mill:Q) | — | 0.0569 | 0.0679 | 0.0617 | 0.1104 |
| (Solution Concentrated to 125 Times) Hydrogen Radical Concentration (μM) | — | 17 | 11 | 8 | 34 |

The embodiment and Examples disclosed this time must be considered as illustrative in all points and not restrictive. The scope of the present invention is shown not by the above description but by the scope of claim for patent, and it is intended that all modifications within the meaning and range equivalent to the scope of claim for patent are included.

INDUSTRIAL APPLICABILITY

When employing the aforementioned method of detecting hydrogen radicals and the aforementioned quantitative analysis method, presence of a small quantity of hydrogen radicals in water or an aqueous solution can be detected and the concentration thereof can also be correctly measured. In particular, the concentration of hydrogen radicals in electroreduction water can be readily and correctly determined by employing this analysis method. Therefore, this analysis method can be applied to uses of various types of products in the medical field, the food field, the beverage field and the like, and electroreduction water can be prepared by adjusting the concentration of hydrogen radicals (active hydrogen) in response to the uses. The method can also be utilized for evaluating the performance of a hydrogen storage alloy.

The invention claimed is:

1. A method of detecting hydrogen radicals present in water or an aqueous solution which comprises the steps of: adding sodium salt of 3,5-dibromo-4-nitrosobenzenesulfonic acid (DBNBS) to a sample such that color results from an absorption peak of a DBNBS azo compound formed by reaction between the sodium salt of DBNBS and the hydrogen radicals; and detecting hydrogen radicals in said sample by detecting an absorption peak at a wavelength of 425 to 450 nm in said sample.

2. The method of detecting hydrogen radicals according to claim 1, wherein the water or the aqueous solution is produced during an electroreduction reaction.

3. A quantitative analysis method for hydrogen radicals present in water or an aqueous solution, consisting of the following steps (1) to (5):

(1) blowing hydrogen gas into a solution of 1,1-diphenyl-2-picrylhydrazyl (DPPH) having absorption in the vicinity of 517 nm at a constant speed in the presence of platinum black and measuring absorbance of DPPH at multiple points over a period of time to determine a correlation between a decrease in absorbance in the vicinity of 517 nm and the amount of time that the hydrogen gas was blown into the solution which may be represented as calibration curve A;

(2) reacting cysteine with DPPH and measuring both absorbance of DPPH and concentration of cysteine at multiple points over a period of time to determine a correlation between a decrease in absorbance by DPPH in the vicinity of 517 nm and cysteine concentration which may be represented by calibration curve B;

(3) calculating a correlation of hydrogen radicals formed per unit of blowing time of the hydrogen gas based on calibration curve A and calibration curve B;

(4) blowing hydrogen gas into a solution of sodium salt of 3,5-dibromo-4-nitrosobenzenesulfonic acid (DBNBS) at a constant speed in the presence of platinum black under the same conditions as in said step (1) and thereafter measuring absorbance in the vicinity of 450 nm at multiple points over a period of time to determine a correlation between the value of the absorbance and the concentration of hydrogen radicals formed per unit of blowing time of the hydrogen gas calculated based on calibration curve A and calibration curve B which may be represented as calibration curve C; and (5) adding sodium salt of DBNBS to a sample and measuring absorbance in the vicinity of 450 nm to determine the concentration of the hydrogen radicals from the value of said absorbance based on calibration curve C.

* * * * *

UNITED STATES PATENT AND TRADEMARK OFFICE
CERTIFICATE OF CORRECTION

PATENT NO. : 7,276,379 B2
APPLICATION NO. : 10/344341
DATED : October 2, 2007
INVENTOR(S) : Sanetaka Shirahata et al.

It is certified that error appears in the above-identified patent and that said Letters Patent is hereby corrected as shown below:

Title Page, item (75) should read as follows:
(75) Inventors: Sanetaka Shirahata, Fukuoka (JP); Kazumichi Otsubo, Osaka (JP)

Signed and Sealed this

Third Day of November, 2009

David J. Kappos
*Director of the United States Patent and Trademark Office*